United States Patent [19]

Tanigaki

[11] Patent Number: 5,637,870
[45] Date of Patent: Jun. 10, 1997

[54] METHOD OF ANALYSIS OF DISTRIBUTION OF CONCENTRATION OF SUBSTRATE

[75] Inventor: Takeshige Tanigaki, Tokyo, Japan

[73] Assignee: Sony Corporation, Tokyo, Japan

[21] Appl. No.: 575,592

[22] Filed: Dec. 20, 1995

[30] Foreign Application Priority Data

Dec. 22, 1994 [JP] Japan .................. 6-319631

[51] Int. Cl.$^6$ .............. H01J 37/28; H01J 49/00; B01D 59/44
[52] U.S. Cl. .............. 250/307; 250/282; 250/309
[58] Field of Search .............. 250/282, 307, 250/309, 397, 492.21

[56] References Cited

U.S. PATENT DOCUMENTS

| | | | |
|---|---|---|---|
| 3,840,743 | 10/1974 | Tamura et al. | 250/307 |
| 4,510,387 | 4/1985 | Izumi et al. | 250/309 |
| 4,835,115 | 5/1989 | Eklund | 437/38 |
| 5,350,919 | 9/1994 | Hirano et al. | 250/282 |
| 5,442,174 | 8/1995 | Kataoka et al. | 250/309 |
| 5,502,305 | 3/1996 | Kataoka | 250/309 |
| 5,521,377 | 5/1996 | Kataoka et al. | 250/309 |

*Primary Examiner*—Bruce C. Anderson
*Attorney, Agent, or Firm*—Hill, Steadman & Simpson

[57] ABSTRACT

A method of analysis of the distribution of concentration of a substrate including: a step of preparing a plurality of types of sample substrates whose distribution of concentration is to be analyzed; a step of forming on the surfaces of those substrates dummy films of a material different from the substrates or etching the surfaces of the plurality of sample substrates to different depths; in the case of the dummy films; a step of introducing into the sample substrates specific impurities from the direction of the dummy films under substantially identical conditions and then a step of removing the dummy films; a step of performing mass analysis from the sides of the sample substrates; and a step of sequentially calculating the difference in the results of the mass analysis among the sample substrates.

12 Claims, 5 Drawing Sheets

METHOD OF ANALYSIS OF DISTRIBUTION OF CONCENTRATION OF SUBSTRATE

BACKGROUND OF THE INVENTION

1. Field of the Invention

The present invention relates to a method of analysis of the distribution of concentration in a substrate, more particularly relates to a method of analysis of the distribution of concentration in a semiconductor substrate which enables an accurate analysis of not only the distribution Of concentration of specific atoms in the depth direction of the semiconductor substrate, but also the distribution of concentration in the horizontal direction of the semiconductor substrate.

2. Description of the Related Art

The SIMS method of analysis offers a ultrahigh sensitivity (down to the ppb level) and a high depth-resolution (down to 1 nm). The SIMS method is being taken note of in the field of semiconductors, for example, as the most effective method of analysis when determining the distribution of concentration of doping impurities in ultra shallow regions resulting from ultra low energy ion implantation.

In the SIMS method, a finely focused primary ion beam is irradiated on the surface of a sample to drive out atoms from inside the sample. The group of ionized particles forming part of this, that is, the secondary ions, are analyzed in mass spectrometer. Normally, the energy of the primary ions used is several keV to 20 keV or so where the sputtering efficiency is high. The primary ions used are $O_2^+$, $Cs^+$, $Ar^+$, $Ga^+$, etc.

The lateral resolution of SIMS instruments, however, is heavily dependent on the operating principles of the instrument and the conditions of the analysis. Even when finely adjusting the factors of the instrument well, it is at most several microns to 10 or so microns. Therefore, it has been almost impossible to analyze the concentration of impurities distributed in a region of less than the submicron size, such as the lateral spread from an ion implanted region, directly at the surface from above the sample.

It has been proposed to perform some sort of processing when using the SIMS method to analyze the concentration of impurities distributed in regions of less than the submicron size. The methods tried in the past may be roughly grouped into the following two types:

The first type of method is the method described in J. Vac. Sci. Technol. B, Vol. 10, No. 1, Jan/Feb. 1992, pp. 353 to 357. In this method, a plurality of parallel etched grooves are formed by dry etching so as to cross at an extremely fine angle (θ=0.08° to 0.1°) the longitudinal direction of a plurality of stripe-like ion-implanted regions. The depth of each groove is made somewhat deeper than the main region of distribution of the implanted impurities. Next, to avoid a shape effect at the time of SIMS analysis, use is made of semiconductor planarization to bury the grooves by a material such as polycrystalline silicon. The original surfaces of the implanted substrate adjoining the edges of the grooves of the sample obtained in this way are analyzed point-wise by successively shifting the ion beam or the sample stage in the direction of the grooves.

In this method, dependent upon the cross angle θ, the real distance in the lateral direction ΔX is projected magnified along the edge lines of the etched grooves and the resolution is improved. For example, it is increased about 800- to 1000-fold when 1=ΔX/sinθ and θ=0.08 to 0.1.

In this first method, however, even if the ion beam is focused to a spot of at most 10 μm, which is the practical effective diameter, a lateral resolution of only 0.01 to 0.0125 μm can be obtained when converted to real distance in the lateral direction. For example, if ΔX=0.1 μm, when projected, it becomes 1=80 to 100 μm. The analysis points are at most split into 8 to 10 points.

Further, in the first method, processing of the samples requires sophisticated and complicated semiconductor processing techniques such as photolithography, dry etching, and planarization and, further, time is taken for the preparation of the samples.

Further, in the first method, it is difficult to judge with a high degree of precision the cross points between the boundaries between the ion-implanted regions and non-implanted regions and the stripes of the etched grooves. In the end, it is difficult to maintain a high absolute positional precision for the analysis of the distribution of concentration in the lateral direction. Further, even assuming analysis under the identical conditions at different analysis points, accurate determination of the initial position of depth from the surface is extremely difficult.

The second method is the method proposed by R. von Criegern et al. of Siemens Co. In this method, the side face of a sample in which ions have been implanted is cut in a direction substantially perpendicular to the surface of the sample and SIMS depth profiling is performed perpendicularly with respect to this face. This second method as well enables measurement of the distribution of impurities caused by ion implantation in the lateral direction since it calls for SIMS analysis from the side face of the sample.

However, in this method, it is necessary to cut and polish the side face of the sample, so special tools are required for the polishing.

Further, in the second method, since SIMS depth profiling is performed, a sub-nanometer level (less than 1 nm) of resolution is required, so it is not possible to use a point-like ion beam. Beam scanning such as raster scanning of a certain surface region (for example, 100×100 μm or 500× 500 μm) is essential. Accordingly, despite the fact that the doping impurities form a certain gradient of concentration with respect to the direction of ion implantation even directly below the mask in the same way as the region directly under the ion implantation windows, it is not possible to resolve and capture that state of distribution. That is, in the conventional second method, the state of distribution of concentration of the impurities diffused and distributed in the lateral direction was just integrated with respect to the direction of implantation.

Note that there are other methods of analyzing the distribution of concentration other than the SIMS method.

The level of concentration of impurities diffused and redistributed from the ion implantation to a region under the mask is dependent on the implanted dosage, the annealing conditions, etc. but is about $10^{13}$ to $10^{17}$ atoms/cm$^3$. Even directly under a mask edge at a depth of the projected range (Rp), it is at most no more than $10^{19}$ atoms/cm$^3$. Accordingly, with physical analytical techniques other than the SIMS method (XPS, AES, RBS, EPMA-WDX/EDX, etc.), the concentration is below all of their detectable limits and therefore analysis is impossible. Methods tried in the past other than analytical techniques have been the transmission electron microscope (TEN) method, the scanning tunnel microscope (STM) method, etc. Each of these methods evaluate the pn junction regions from the perpendicular cross-sections. The features and problems of these will be pointed out briefly below.

In the method of selective etching and TEM examination of the cross-section, the perpendicular cross-section of the implanted region is chemically etched for selective etching dependent on the level of concentration of the impurities. Naturally, continuous contours of concentration are formed along the regions of both the implantation windows and implantation mask. It is possible to examine this pattern of etching at a high magnification by a transmission electron microscope.

This technique requires sophisticated technology in fabricating ultra thin film samples for the TEM examination and further it is difficult to handle the results of the examination quantitatively. It is superior as a method of qualitative examination however.

In ultrahigh vacuum STM measurement using a scanning tunnel microscope, the pn junction surface is sliced open and exposed under an ultrahigh vacuum (UHV) (or in the atmosphere) and the STM chip is scanned two-dimensionally. The in-plane resolution of the probe is a comparatively high 10 nm, but the quantitative relationship between the tunnel current and the impurity concentration is not yet clear.

SUMMARY OF THE INVENTION

The present invention was made in consideration of the above situation and has as its object to provide a method of analysis of the distribution of concentration of a substrate which enables an accurate analysis of not only the distribution of concentration of specific atoms in the depth direction of the substrate, but also the distribution of concentration in the horizontal direction of the substrate.

To achieve the above object, according to a first aspect of the invention, there is provided a method of analysis of the distribution of concentration of a substrate including: a step of forming on surfaces of substrates whose distribution of concentration is to be analyzed dummy films of a material different from the substrates to prepare a plurality of types of sample substrates on which dummy films of different thicknesses are formed; a step of introducing into the plurality of types of sample substrates specific impurities from the direction of the dummy films under substantially identical conditions; a step of removing the dummy films present on the surfaces of the sample substrates at which the impurities have been introduced; a step of performing mass analysis from the sides of the sample substrates from which the dummy films have been removed; and a step of sequentially calculating the differences in the results of the mass analysis among sample substrates on which the dummy films of different thicknesses had been formed.

Preferably, the method further includes a step of forming on the surfaces of the sample substrates from which the dummy films have been removed buffer films of a material different from the sample substrates and performs the mass analysis from the sides of the sample substrates on which the buffer films have been formed.

According to a second aspect of the invention, there is provided a method of analysis of the distribution of concentration of a substrate including: a step of preparing a plurality of types of sample substrates whose distribution of concentration of the substrate is to be analyzed; a step of etching surfaces of the plurality of sample substrates to different depths; a step of performing mass analysis from the sides of the sample substrates; and a step of sequentially calculating the differences in the results of the mass analysis among sample substrates having surfaces etched to different depths.

Preferably, the method further includes a step of forming on the surfaces of the sample substrates which have been etched buffer films of a material different from the sample substrates and then performs the mass analysis from the sides of the sample substrates on which the buffer films have been formed.

Preferably, the means for introducing the impurities at the surfaces of the sample substrates is ion implantation.

Preferably, the dummy films are comprised of a material which has a larger selectivity at the time of etching than the substrates and further gives rise to a phenomenon of introduction of impurities substantially the same as the substrates when introducing the impurities.

The substrates may for example be monocrystalline silicon substrates, and the dummy films may be comprised of silicon oxide films formed by thermal oxidation.

The buffer films may be comprised of polycrystalline silicon films.

The method of mass analysis may be the secondary ion mass analysis method.

BRIEF DESCRIPTION OF THE DRAWINGS

The present invention will be more fully understood from the description of the preferred embodiments of the invention set forth below, together with the accompanying drawings, in which.

DESCRIPTION OF THE PREFERRED EMBODIMENTS

Figure 1:
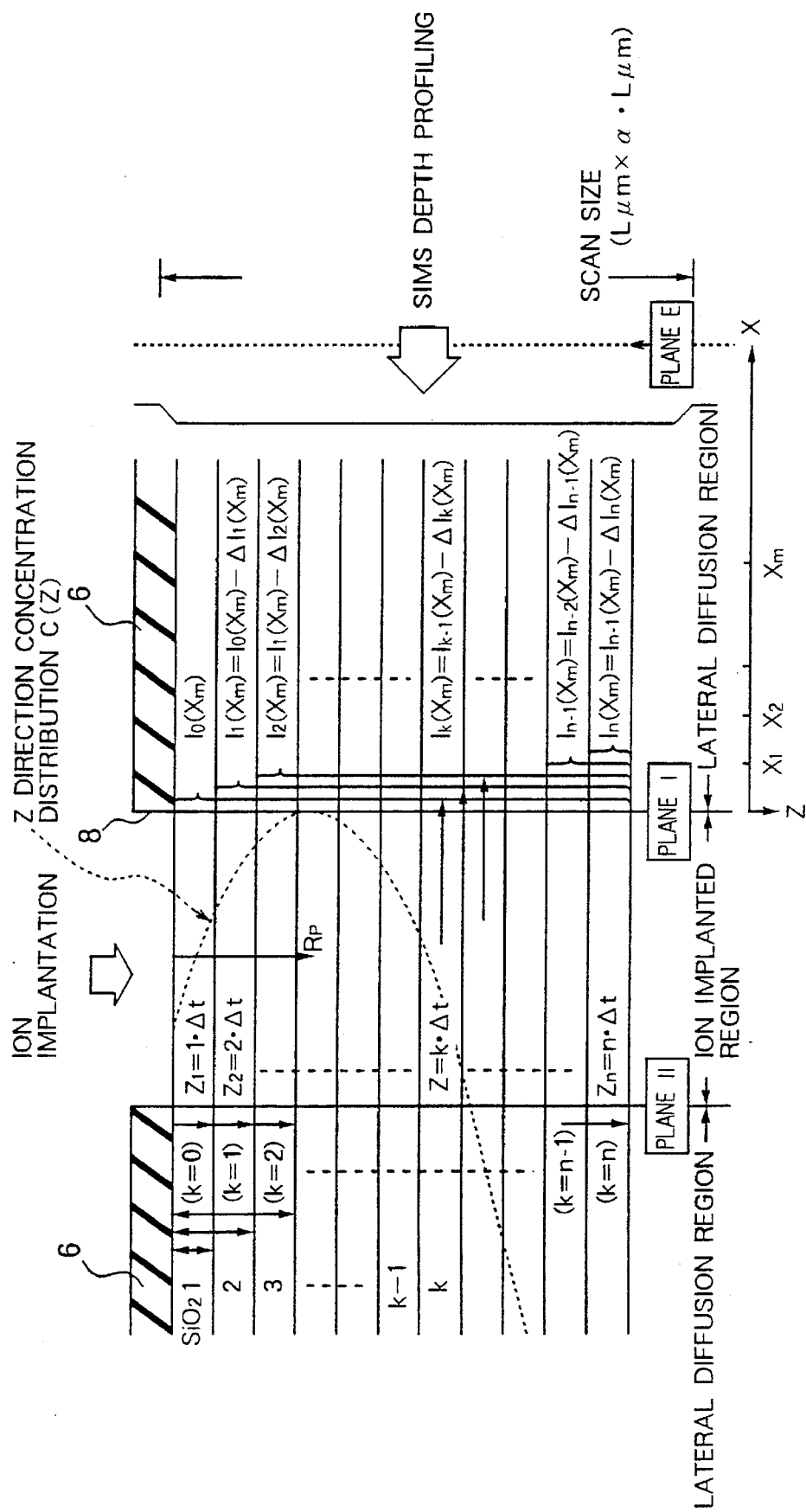
FIG. 1 is an explanatory view of key points in the method of analysis of the distribution of concentration according to one embodiment of the present invention.

In the method of analysis of the distribution of concentration of a substrate according to the first aspect of the present invention, n+1 number of sample substrates on which dummy films of thicknesses of $\Delta t \times k$ ($k=0, 1, 2 \ldots n$) nm are formed are prepared. On the surfaces of the dummy films of the sample substrates are formed ion implantation masks of the same conditions as of fabrication of an actual device (for example, ion implantation resist masks). In this case, for the shapes of the windows, the widths are made equal to those at the time of fabrication of the actual device and the lengths of the windows are made semi-infinite to forms stripes. Impurities are introduced from these windows into the sample substrates under identical conditions by ion implantation etc.

On the other hand, the main regions of distribution of the implanted impurities may be considered to be the regions of $k_o \times Rp$ ($k_o=2$ to 5) in the direction directly under the implantation windows, where Rp is the projected range at the time of the ion implantation, so $\Delta t$ is determined using $k_o \times Rp/N$ (N is 20 or so) as a yardstick. $\Delta t$ is preferably as small as possible from the viewpoint of improvement of precision, but is dependent on the technique used for forming the dummy films so is for example 1 nm or so. The thicknesses of the dummy films formed on the sample substrates have to be measured in advance by an ellipsometer etc. (even if not measured, the thicknesses of the films should be evaluated experimentally by correlative data with the formation conditions). The maintenance of the precision of the thickness of the dummy films to the nanometer level is one of the key points of the present invention.

The dummy films are comprised of a material which has a larger selectivity at the time of etching than the substrates and further gives rise to a phenomenon of introduction of impurities substantially the same as the substrates when introducing the impurities. For example, when the substrates are monocrystalline silicon substrates, the dummy films are preferably silicon oxide films. These two substances can be deemed to be almost equivalent in terms of the implantation phenomenon due to the equivalence in nuclear stopping power and electronic stopping power regardless of the species of the ion implanted impurity or the implantation energy. This is also one of the key points of the present invention.

Next, the impurity introduction masks are removed and then the dummy films are removed. By removing the dummy films, the impurities introduced into them are also removed. Next, buffer films are formed on the surfaces of the substrates from where the dummy films had been removed. The thicknesses of the buffer films may all be substantially the same. The thickness is for example several microns. The buffer films are not particularly limited. For example, use may be made of polycrystalline silicon. By forming the buffer films, it is possible to prevent to a great extent the polishing overhang at the corners of the original substrate surfaces and side edges when polishing the side faces of the substrates in the back end processes.

Next, the side edge faces of the sample substrates processed in this way (side edge faces substantially perpendicular to the surfaces of the substrates), that is, the parallel side edge faces along the longitudinal direction of the windows of the impurity introduction masks are cut and polished. To avoid an uneven etching effect in the plane or in the direction of depth at the time of the SIMS depth profiling, it is important that the side edge faces be finished to about the degree of the mirror surface of a usual semiconductor wafer.

SIMS Analysis

Next, in the present invention, mass analysis is performed from the polished side edge faces of the thus prepared (n+1) number of sample substrates. The mass analysis used is for example the SIMS method. In the SIMS method, a primary ion beam is irradiated and SIMS depth profiling performed by the following procedure:

[1] Method of Irradiation of Primary Ion Beam

To perform depth profiling while holding the resolution in the depth direction to about 0.01 nm, a wide raster scan (L $\mu m \times L$ $\mu m$) of a primary ion beam is necessary. For example, n is made 500 $\mu m$. However, since the region currently under note (thickness of the impurity diffusion layer from the ion implanted layer) is remarkably thin, the aperture size is set sufficiently large compared with the raster size. For example, the raster size is made 0.9 L×0.9 L or the analysis is performed without an aperture.

[2] Method of Sampling

When irradiating the primary ion beam by the raster scan, it is preferable that the stage supporting the substrate be moved linearly reciprocally over the scan direction. The direction of the linear reciprocal movement is substantially parallel to the direction of the stripe windows in the impurity introduction masks. The reciprocal distance of the linear reciprocal movement is preferably a distance of a maximum 5 to 10 times the raster scan size L.

The specific secondary ion intensity (I) of the impurity element being studied is measured between the turning points of the linear reciprocal movement.

Note that to maintain an excellent depth resolution, the impurity element is preferably limited to a single type. Further, it is preferable to select a separate single monitor ion species. However, it is also possible to simultaneously analyze a plurality of impurity elements.

This sampling method, compared with the sampling method using a raster scan in a single fixed region, gives a broader range of actual scanning and thereby an improved sensitivity of analysis in measurement assuming the following (i) and (ii):

(i) There is no gradient of concentration of the impurities formed in the longitudinal direction of the implantation windows (stripes).

(ii) The diffusion coefficient is independent on the concentration in the case of the diffusion of impurities from the regions directly under the implantation windows to regions directly under the implantation masks.

[3] Method of Setting Raster Scan Region

The region irradiated by the raster scan of the primary ion beam is preferably not only the side edge faces of the sample substrates. Preferably part also covers the regions of the buffer films. Due to this, it is possible to analyze without any omission the distribution of concentration of impurity elements diffused near the substrate surfaces directly under the impurity introduction masks. Note that in the present invention, by performing the SIMS depth profiling from the side edge faces of the sample substrates, it is possible to suppress to a great degree the crater peripheral effect inherent to SIMS and thereby improve the precision of analysis.

Processing After or Simultaneous With SIMS Analysis

After the SIMS analysis of the (n+1) number of sample substrates or simultaneously with that analysis, processing is performed to find the two-dimensional distribution of concentration based on the following expression:

If the integral of the secondary ion intensity obtained as a result of the SIMS analysis of the (n+1) number of sample substrates is $I_k(X_m)$, then the following expression (1) is generally maintained:

$$I_k(X_m) = I_{k-1}(X_m) - \Delta I_k(X_m) \qquad (1)$$

Here, k shows the k-th sample substrate, while $X_m$ shows the distance in the depth direction in the SIMS analysis. Further, $\Delta I_k(X_m)$ is the difference in secondary ion intensities between two sample substrates (k−1, k).

The following expression (2), equivalent to the above expression (1), stands:

$$I_o(X_m) = I_n(X_m) + \sum_{k=1}^{n} \Delta I_k(X_m) \qquad (2)$$

In the SIMS method, measurement of the secondary ion intensity is possible over an extremely broad range (dynamic range of $10^0$ to $10^6$). Accordingly, the difference $\Delta I_k(X_m)$ can be detected as a significant quantity.

On the other hand, in general, the secondary ion intensity ($\Delta I_j$) of a specific mass of a J-th element present in a microspace of a certain solid sample is given by the following expression (3):

$$\Delta I_j \eta \cdot S \cdot Y_j \cdot C_j \cdot I_p \qquad (3)$$

Here, $I_p$ is the primary ion current and $\eta$ and S are the secondary ion transmittance and sputtering ratio. Further, $Y_j$ and $C_j$ are the secondary ion yield rate and concentration of atoms of the element (J).

By keeping the SIMS depth profiling conditions for the (n+1) types of samples constant, since the $\eta$, S, $Y_j$, and $I_p$ in the above expression (3) are all constant values, the concentration of atoms $C_j$, which is the object of the analysis, maintains a linear relationship with the secondary ion intensity $\Delta I_j$. That is, $C_j = K \times \Delta I_j$, where the proportional coefficient K is determined using standard samples of known concentrations.

By going through the above analysis procedure, it is possible to analyze two-dimensionally the distribution of concentration of doping impurities cutting across the perpendicular faces I and II directly below the mask edges and laterally diffusing in the regions under the masks.

That is, the differences between the secondary ion intensities $I_k(X_m)$ and $I_{k-1}(X_m)$ measured between two adjoining samples are found for each specific position (X) sequentially between (n, n−1)→(n−1, n−2)→... →(2, 1)→(2, 1)→(1, 0) (n number for each m value). The differences $I_k(X_m)$ are secondary ion intensities corresponding to the concentrations of impurities at the lateral coordinate $X_m$ and depth coordinate Z. Accordingly, by converting these to concentrations based on the above expression (3) and plotting them two-dimensionally on an (X,Z) plane, a graph of the two-dimensional distribution of concentration of C (X,Z) is obtained. Here, the relationship of $Z = Z_n = (n-k) \times \Delta t$ is held, where, k=0, 1, 2, ... n.

By using the method of the present invention, it is possible to secure a resolution of the spatial distribution on the level of $\Delta X = 0.02$ to 0.10 nm and $\Delta Z = 1$ nm as maximum values with respect to the lateral direction (X) and longitudinal direction (Z, ion implantation direction).

The second aspect of the method of analysis of distribution of concentration according to the present invention differs from the method of the first embodiment explained above in only the following points. The rest of the technique is the same, so explanations of overlapping portions will be omitted.

In this aspect of the invention, instead of preparing a plurality of sample substrates on which dummy films of different thicknesses are formed, a plurality of sample substrates on which no dummy films are formed are prepared.

Impurities are introduced into these sample substrates under identical conditions, then the surfaces of the substrates at the sides where the impurities were introduced are etched to different depths. Next, according to need, buffer films are formed on the surfaces of the sample substrates, then SIMS depth profile analysis and then computation are performed in the same way as the first method explained above.

In this method, the point is that the surfaces of the plurality of sample substrates are etched to depths of a high precision.

The method according to the second embodiment of the present invention has similar functions as explained above.

Next, the method of analysis of the distribution of concentration according to the present invention will be explained in further detail based on embodiments shown in the Figures.

Figure 2:
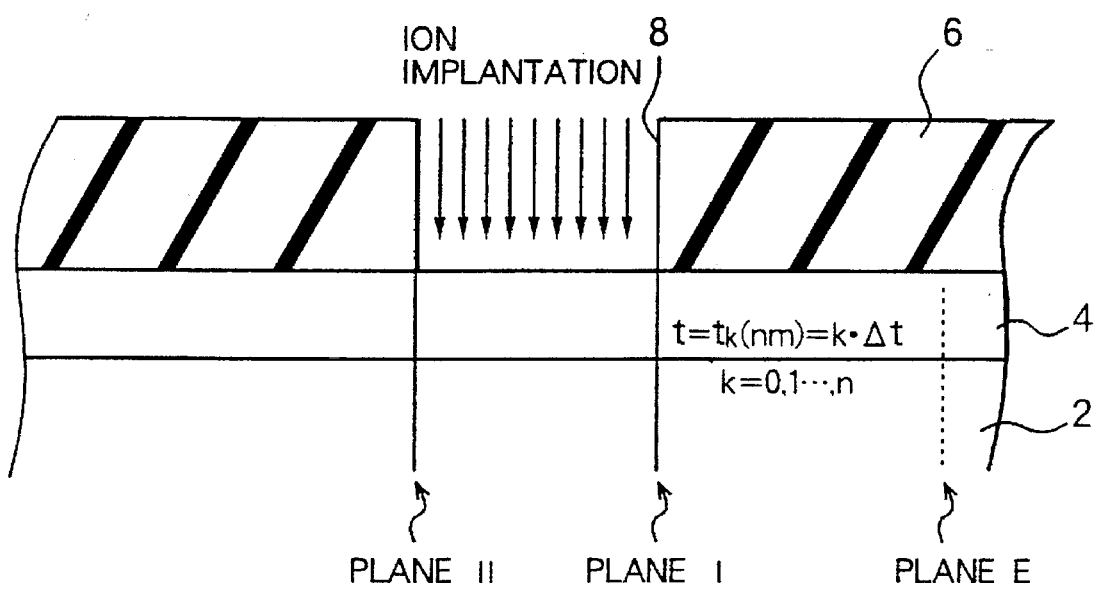
FIG. 2 is a cross-sectional view of key portions of a sample substrate at the time of introduction of impurities.
Figure 3:
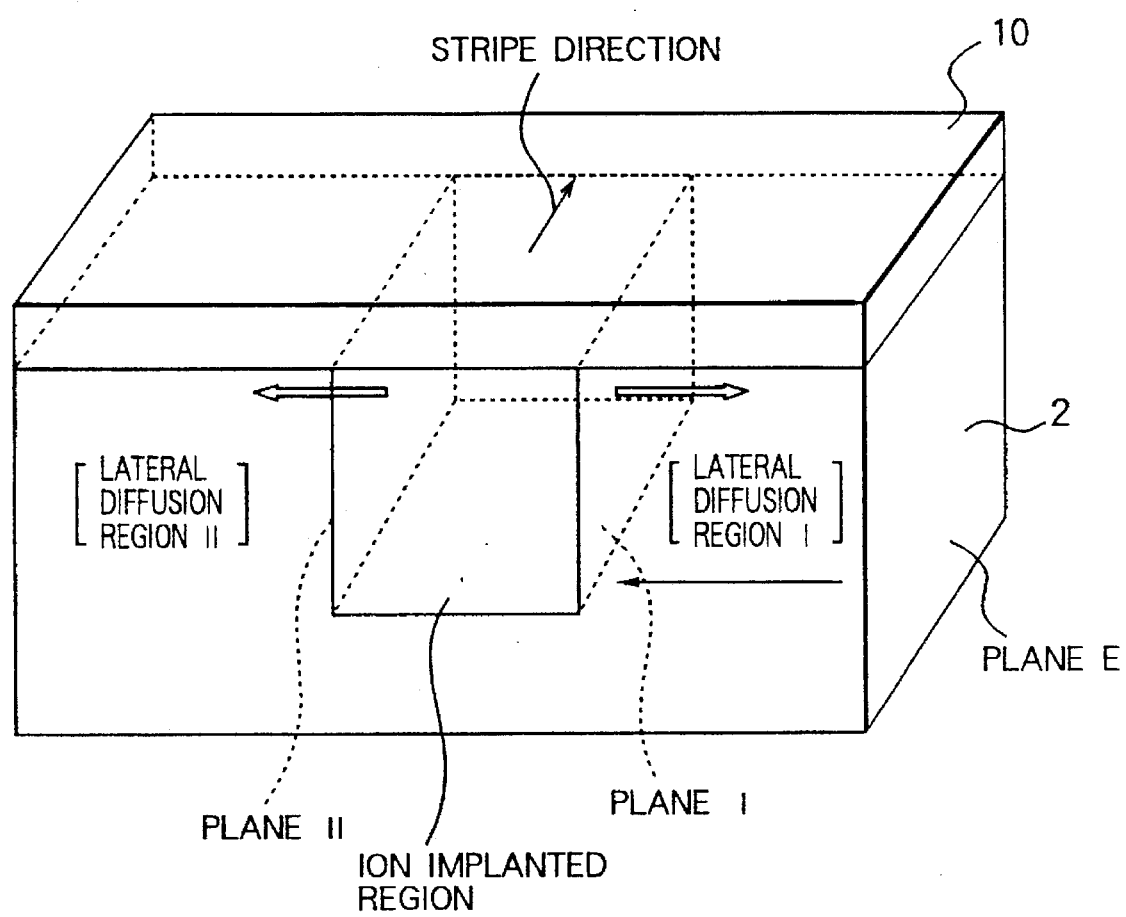
FIG. 3 is a partially cut-away perspective view of a sample substrate.
Figure 4:
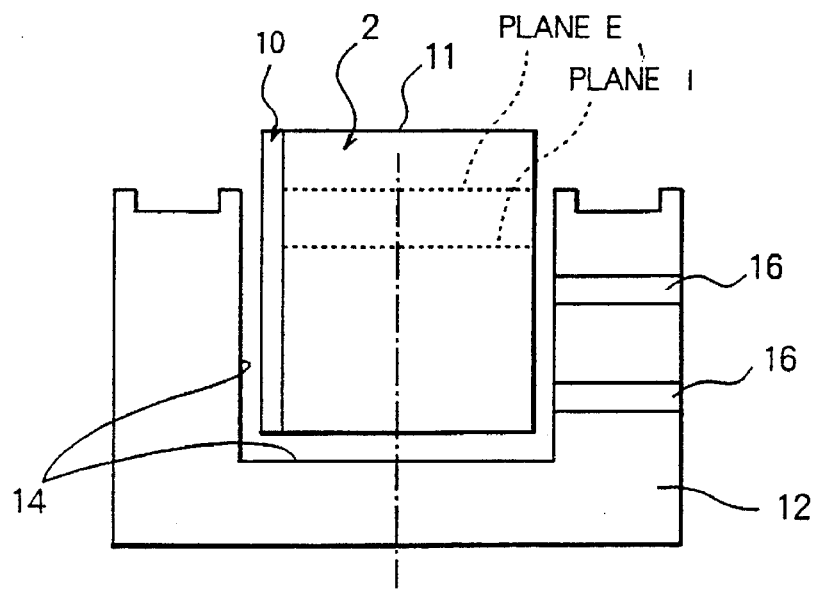
FIG. 4 is a cross-sectional view of a holder for holding a sample substrate for polishing the side edge of the substrate.
Figure 5:
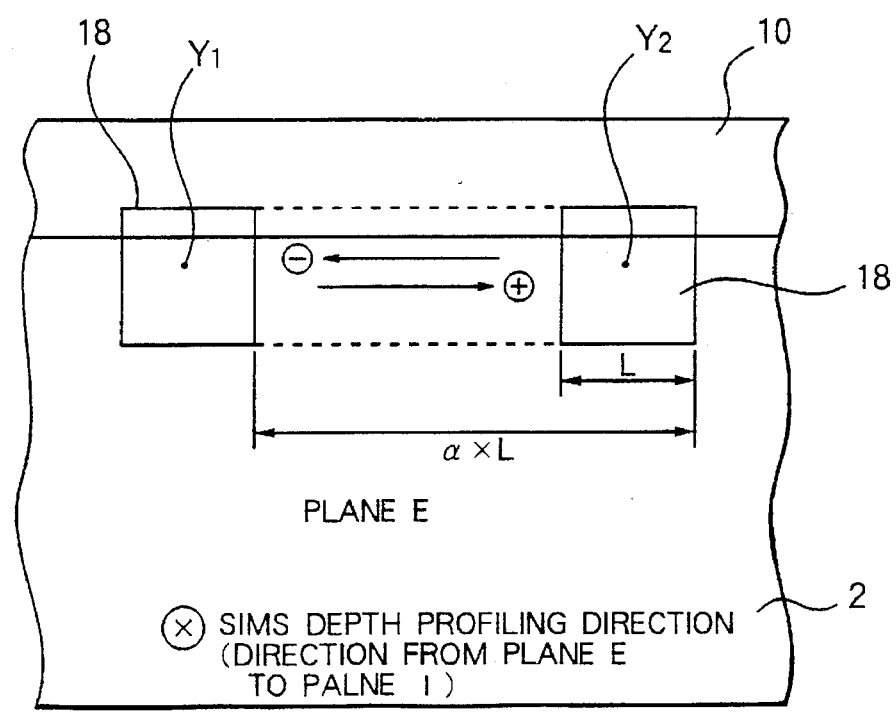
FIG. 5 is a view of showing the relationship between a raster-scanning size of a primary ion-beam and the reciprocal-linear movement of the substrate.

As stated above, FIG. 1 is an explanatory view of key points in the method of analysis of the distribution of concentration according to one embodiment of the present invention, FIG. 2 is a cross-sectional view of key portions of a sample substrate at the time of introduction of impurities, FIG. 3 is a partially cut-away perspective view of a sample substrate, FIG. 4 is a cross-sectional view of a holder for holding a sample substrate for polishing the side edge of the substrate, and FIG. 5 is a perspective view of a sample substrate.

First Embodiment

In this embodiment, first, as shown in FIG. 2, n+1 number of sample substrates 2 on which dummy films 4 of thicknesses of $\Delta t \times k$ (k=0, 1, 2. . . n) nm are formed are prepared. In this embodiment, as the sample substrates 2, use is made of monocrystalline silicone wafers. The dummy films 4 formed on these sample substrates 2 are comprised for example of silicon oxide films. Dummy films 4 comprised of silicon oxide films are formed by thermal oxidation of the surfaces of the silicon substrates. The thicknesses of the dummy films 4 are controlled by controlling the thermal oxidation conditions. To have the difference in thickness $\Delta t$ of the dummy films 4 formed on the surfaces of the different sample substrates 2 be as small as possible is preferable from the viewpoint of improving precision, but this is dependent on the technique used for forming the dummy film so is for example 1 nm or so. The thicknesses of the dummy films 4 formed on the sample substrates 2 are preferably measured in advance by an ellipsometer, X-ray photoelectron spectrometer (XPS), etc. The maintenance of the precision of the thickness of the dummy films to the nanometer level is one of the key points of the present invention. Note that when k=0, sometimes no dummy film comprised of a silicon oxide film is formed on the surface of the substrate 2.

The dummy films 4 are comprised of a material which has a larger selectivity at the time of etching than the substrates 2 and further gives rise to a phenomenon of introduction of impurities substantially the same as the substrates 2 when introducing the impurities. From this viewpoint, in this embodiment, the dummy films 4 used are silicon oxide films. Silicon and silicon oxide can be deemed to be almost equivalent substances with respect to the implantation phenomenon due to the equivalence in nuclear stopping power and electronic stopping power regardless of the species of the ion implanted impurities or the implantation energy. This is also one of the key points of the present invention.

Next, as shown in FIG. 2, on the surfaces of the dummy films 4 of the sample substrates 2 are formed ion implantation resist masks 6 of the same conditions as of fabrication of an actual device. In this case, for the shapes of the windows 8 of the resist masks 6, the widths are made equal to those at the time of fabrication of the actual device and the lengths of the windows 8 are made semi-infinite to forms tripes.

Impurities are introduced from these windows 8 into the sample substrates 2 under identical conditions by ion implantation. The impurities are introduced into the surfaces of the dummy films 4 and the substrates 2 from the windows 8 shown in FIG. 2 by the ion implantation.

On the other hand, the main regions of distribution of the implanted impurities may be considered to be the regions of $k_o \times Rp$ ($k_o$=2 to 5) in the direction directly under the implantation windows, where Rp is the projected range at the time of the ion implantation, so $\Delta t$ is determined using $k_o \times Rp/N$ (N is 20 or so) as a yardstick. $\Delta t$, as mentioned earlier, is preferably as small as possible from the viewpoint of improvement of precision, but is dependent on the technique of formation of the dummy films and for example is 1 nm or so.

Next, the resist films 6 of the sample substrates 2 are removed and then the dummy films 4 are removed. By removing the dummy films 4, the impurities introduced into them are also removed. Next, as shown in FIG. 3, buffer films 10 are formed on the surfaces of the substrates 2 from where the dummy films 4 had been removed. The thicknesses of the buffer films 10 may all be substantially the same for the sample substrates 2. The thickness is for example several microns. The buffer films 10 are not particularly limited. For example, use may be made of polycrystalline silicon. By forming the buffer films 10, it is possible to prevent to a great extent the polishing overhang at the corners of the original substrate surfaces and side edges when polishing the side faces of the substrates 2 in back end processes. Next, the side edge faces of the sample substrates 2 processed in this way (side edge faces substantially perpendicular to the surfaces of the substrates), that is, the parallel side end faces 11 along the longitudinal direction of the windows 8 of the resist masks 6 (see FIG. 4), are cut and polished until the plane E (see FIGS. 3, 4, 5, and 6). To avoid an uneven etching effect in the plane or in the direction of depth at the time of the SIMS depth profiling and maintain a depth resolution of the 0.01 to 0.1 nm level, it is important that the side edge faces 11 be finished to about the mirror surface of a usual semiconductor wafer.

When processing the side edge faces 11, use is made of the chip fixing device 12 shown in FIG. 4. A commercially available polishing apparatus is used to mechanically lap/polish or mechanochemically polish them. When mechanochemically polishing them, use is made for example of an alkaline solution containing a polishing agent comprised primarily of high purity silica particulates as used in SOI techniques etc.

As the fixing device 12, use is made of one with a high precision of processing. The sample substrates 2 are fixed in place by screwing by a screw portion 16 and also providing wax at the inside of the groove 14 so as to prevent loosening, slipping, tilting, etc. at the time of polishing. In normal mechanical polishing, use is made of a 0.06 to 0.1 µm paste and a suitable oil to finish the plane E to a mirror surface.

The processing of the side edge faces 11 of the substrates 2 can be performed using a commercially available polishing apparatus, for example, a sample polishing apparatus used in measurement of spreading resistance. Use may also be made of the apparatus described in Japanese Unexamined Patent Publication (Kokai) No. 5-206090 etc.

At the time of this polishing, in this embodiment, since a buffer film 10 is formed at the surface of the substrate 2, no polishing overhang occurs at the boundary between the substrate 2 and the buffer film 10.

Next, in this embodiment, a primary ion beam is irradiated from the plane E, that is, the polished side edge face, for the (n+1) number of the sample substrates 2 prepared in the above way and SIMS depth profiling is performed by the following manner.

To perform depth profiling while holding the resolution in the depth direction to about 0.01 nm, a wide raster scan of the primary ion beam (L µm×L µm) is necessary. For example, n is made 500 µm. However, since the region currently under note (thickness of the impurity diffusion layer from the ion implanted layer) is remarkably thin, the aperture size is set sufficiently large compared with the raster size. For example, the raster size is made 0.9 L×0.9 L or the analysis is performed without an aperture.

Examples of the measurement conditions for the SIMS method are shown below:

TABLE 1

| SIMS CONDITIONS | | |
|---|---|---|
| Primary ion species | $^{32}O^+$ | $^{32}O^+$ |
| Primary accelerating voltage (kV) | 15 | 15 |
| Primary ion current (nA) | 120 | 140 |
| Raster size (µm²) | 500 × 500 | 500 × 500 |
| Sputter rate (nm/s) | 0.08 | 0.07 |
| Analyzed area (µmφ) | 62 | 62 |
| Detected ion species | $^{11}B^+, ^{29}Si^+$ | $^{75}As^+, ^{29}Si^-$ |
| Analyzed mode | — | Energy offset mode (offset voltage 60 V) |
| Instrument | ims-3F | ims-1F |

Figure 6:
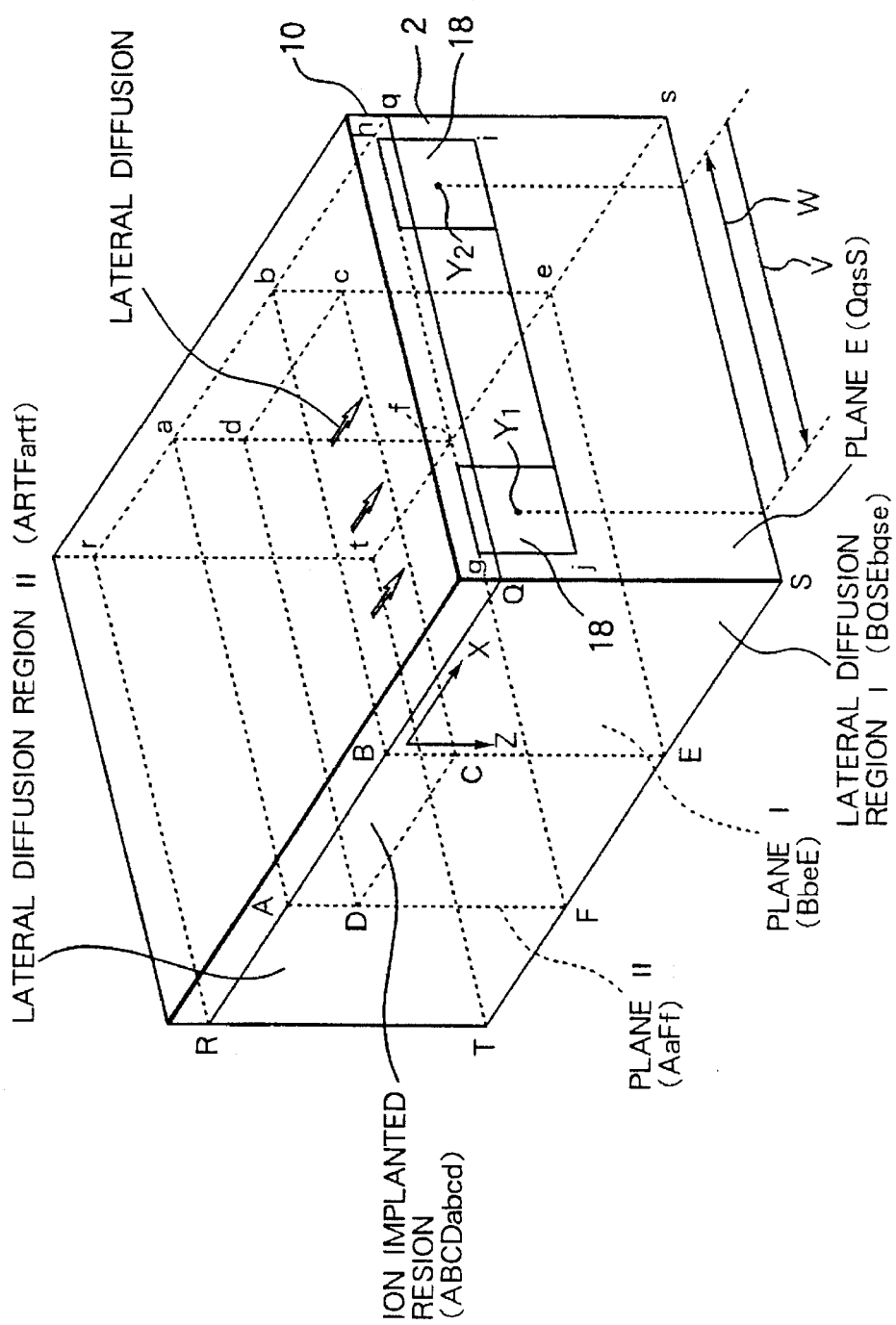
FIG. 6 is a perspective view of a sample substrate.

In this embodiment, when irradiating the primary ion beam by the raster scan, as shown in FIGS. 5 and 6, the stage supporting the sample substrates 2 is moved linearly reciprocally over the scan direction. As shown in FIG. 6, the direction V, W of the linear reciprocal movement of the sample substrates 2 is substantially parallel with the direction of the stripe windows 8 in the resist masks 6 shown in FIG. 2. The reciprocal distance (α×L) of the linear reciprocal movement, as shown in FIG. 5, is preferably a distance of a maximum α=5 to 10 times the raster scan size L. Note that in FIGS. 5 and 6, the areas shown by the reference numerals 18 are the areas of the raster scan by the primary ion beam.

The specific secondary ion intensity (I) of the impurity element being studied is measured between the turning points $Y_1$ and $Y_2$ of the linear reciprocal movement. Note that as shown in FIG. 6, since the substrates 2 are made to move reciprocally in the arrow V and W directions simultaneous with the raster Scan by the primary ion beam, the area actually irradiated by the primary ion beam is the region surrounded by ghij.

Note that to maintain an excellent depth resolution, the impurity element is preferably limited to a single type. Further, it is preferable to select a separate single monitor ion species. However, it is also possible to simultaneously analyze a plurality of impurity elements.

This sampling method, compared with the sampling method using a raster scan in a single fixed region, has a broader range of actual scanning and thereby an improved sensitivity of analysis in measurement assuming the following (i) and (ii):

(i) There is no gradient of concentration of the impurity formed in the longitudinal direction of the implantation windows 8 (stripes).

(ii) The diffusion coefficient is independent on the concentration in the case of the diffusion of impurities from the regions directly under the implantation windows to the regions directly under the implantation masks.

The region irradiated by the raster scan of the primary ion beam is preferably not only the side edge faces of the sample substrates 2. Preferably part also covers the regions of the buffer films 10. Due to this, it is possible to analyze without any omission the distribution of concentration of impurity elements diffused near the substrate surfaces directly under the resist masks 6. Note that in this embodiment, the SIMS depth profiling is performed in a direction X (minus direction) from the plane E, that is, the side end faces of the sample substrates 2, to the plane I. This makes it possible, as a result, to analyze the distribution of impurities from the low concentration region to the high concentration region and thereby to suppress to a great degree the crater peripheral effect inherent to SIMS and thereby improve the precision of analysis.

Note that in FIG. 6, the stripe-like ion implantation region of the surface of the substrate 2 after removal of the dummy film is the region surrounded by ABCDabcd. The plane I (BbeE) and the plane II (AafF) are the planes corresponding to the edges of the window 8 of the resist film 8 shown in FIG. 2. The impurities are diffused and distributed in the depth direction Z as well in the ion implanted region, but pass over the planes I and II and diffuse in the lateral direction X as well. The method of the present embodiment, as explained later, finds the distribution of concentration of impurities in the depth direction Z and the lateral direction X of the substrates 2 to a high precision, so is excellent as a method of analysis.

In this embodiment, after the SIMS analysis of the (n+1) number of sample substrates 2 or simultaneously with that analysis, processing is performed to find the two-dimensional distribution of concentration based on the following expression:

If the integral of the secondary ion intensity obtained as a result of the SIMS analysis of the (n+1) number of sample substrates 2 is $I_k(X_m)$, then the following expression (1) is generally maintained:

$$I_k(X_m) = I_{k-1}(X_m) - \Delta I_k(X_m) \tag{1}$$

The above expression stands in the case of integrals of both one-way or two-way movement between the two points $(Y_1, Y_2)$.

Here, k shows the k-th sample substrate, while $X_m$ shows the distance in the depth direction in the SIMS analysis. Further, $\Delta I_k(X_m)$ is the difference in secondary ion intensities between two sample substrates (k-1, k).

The following expression (2), equivalent to the above expression (1), stands:

$$I_o(X_m) = I_n(X_m) + \sum_{k=1}^{n} \Delta I_k(X_m) \tag{2}$$

In the SIMS method, measurement of the secondary ion intensity is possible over an extremely broad range (dynamic range of $10^0$ to $10^6$). Accordingly, the difference $\Delta I_k(X_m)$ can be detected as a significant quantity.

Note that $X_m = 0$, that is, the interface position where the SIMS profiling cuts across the plane I and enters the ion implanted region, can be determined from where the $I_k(X_m)$ no longer changes and starts to be constant in value for every k-th sample.

On the other hand, in general, the secondary ion intensity $(\Delta I_j)$ of a specific mass of a J-th element present in a microspace of a certain solid sample is given by the following expression (3):

$$\Delta I_j = S \cdot Y_j \cdot C_j I_p \tag{3}$$

Here, Ip is the primary ion current and η and S are the secondary ion transmittance and sputtering ratio. Further, $Y_j$ and $C_j$ are the secondary ion yield and concentration of atoms of the element (J).

By keeping the SIMS depth profiling conditions for the (n+1) types of samples constant, since the η, S, $Y_j$, and $I_p$ in the above expression (3) are all constant values, the concentration of atoms $C_j$, which is the object of the analysis, maintains a linear relationship with the secondary ion intensity $\Delta I_j$. That is, $C_j = K \times \Delta I_j$, where the proportional coefficient K is determined using standard samples of known concentrations.

By going through the above analysis procedure, it is possible to analyze two-dimensionally the distribution of concentration of doping impurities cutting across the perpendicular faces I and II directly below the mask edges and laterally diffusing in the regions under the masks.

That is, as shown in FIG. 1, the differences between the secondary ion intensities $I_k(X_m)$ and $I_{k-1}(X_m)$ measured between two adjoining samples are found for each specific position (X) sequentially between (n, n−1)→(n−1, n−2)→. . . →(2, 1)→(2, 1)→(1, 0) (n number for each m value). The differences $I_k(X_m)$ are secondary ion intensities corresponding to the concentrations of impurities at the lateral coordinate $X_m$ and depth coordinate Z. Accordingly, by converting these to concentrations based on the above expression (3) and plotting them two-dimensionally on an (X,Z) plane, a graph of the two-dimensional distribution of concentration of C (X,Z) is obtained. Here, the relationship of $Z = Z_n = (n-k) \times \Delta t$ is held, where, k=0, 1, 2, . . . n.

By using the method of this embodiment, it is possible to secure a resolution of the spatial distribution on the level of $\Delta X = 0.02$ to $0.10$ nm and $\Delta Z = 1$ nm as maximum values with respect to the lateral direction (X) and longitudinal direction (Z, ion implantation direction).

Second Embodiment

The method of analysis of the distribution of concentration according to the second embodiment of the present invention differs from the method of the first embodiment explained above in only the following points. The rest of the technique is the same, so explanations of overlapping portions will be omitted.

In this embodiment, instead of preparing a plurality of sample substrates on which dummy films of different thicknesses are formed, a plurality of sample substrates 2 on which no dummy films are formed are prepared.

Impurities are introduced into these sample substrates 2 under identical conditions, then the surfaces of the substrates at the sides where the impurities were introduced are etched to different depths. Next, according to need, buffer films 10 are formed on the surfaces of the sample substrates, then SIMS depth profile analysis and then computation are performed in the same way as the first method explained above.

In this method, the point is that the surfaces of the plurality of sample substrates 2 are etched to depths of a high precision.

The method according to the second embodiment of the present invention has similar functions as explained above.

Note that the present invention is not limited to the above embodiments and can be modified in various ways within the scope of the invention.

For example, in the above embodiments, the concentration of impurities introduced by the ion implantation method (perpendicular or slanted) was analyzed, but the present invention is not limited to this and can be applied in exactly the same way to analysis directly under the mask of impurities introduced by the thermal diffusion method. Further, it can be applied to analysis of composition distributed in smaller than submicron dimension microspaces.

Further, in the above embodiments, the secondary ion mass analysis was performed by the SIMS method from the side edges of the substrates 2, but the present invention is not limited to this. As an improvement of the SIMS method, it is also possible to use mass analysis methods such as the sputter-initiated resonance ionization spectroscopy (SIRIS) method, a type of post-ionization (PI)-SIMS method, for example. In the SIRIS method, a sample is irradiated by an ion beam to cause particles to sputter from the surface of the sample, the group of sputtered particles are irradiated with an RIS laser beam in parallel to the surface of the substrate, the neutral particles are post-ionized (PI), the ionized secondary ions are passed through pickup electrodes, an energy filter, and a mass filter and led to a detection system, and then are mass analyzed.

As explained above, according to the present invention, it becomes possible to precisely quantify and analyze the state of two-dimensional distribution of concentration of doping impurities diffused in two-dimensional directions by a simple fabrication of samples and processing with the existing performance of an SIMS instrument or PI-SIMS instrument (in particular the planar resolution).

That is, it is possible to make full use of the two major features of the secondary ion mass analysis method (ultrahigh sensitivity and ultrahigh resolution in depth direction) and analyze the distribution of concentration of any impurity element redistributed in the region directly below the mask in the lateral direction and depth direction by resolutions of about 0.02 to 0.10 nm and 1 nm.

As a result, it becomes possible to provide experimental data for basic studies of the optimization of the design of devices of microdimensions (half/quarter micron level).

Further, it is possible to provide the measurement data, such as diffusion data and data on the distribution of concentration, required for constructing a process simulator. Further, conversely, it is possible to give measurement data for verification of process simulators.

While the invention has been described by reference to specific embodiments chosen for purposes of illustration, it should be apparent that numerous modifications could be made thereto by those skilled in the art without departing from the basic concept and scope of the invention.

What is claimed is:

1. A method of analysis of the distribution of concentration of a substrate including:
    a step of forming on surfaces of substrates whose distribution of concentration of the substrate is to be analyzed dummy films of a material different from said substrates to prepare a plurality of types of sample substrates on which dummy films of different thicknesses are formed;
    a step of introducing into said plurality of types of sample substrates specific impurities from the direction of said dummy films under substantially identical conditions;
    a step of removing said dummy films present on the surfaces of the sample substrates at which said impurities have been introduced;
    a step of performing mass analysis from the sides of the sample substrates from which said dummy films have been removed; and
    a step of sequentially calculating the difference in the results of said mass analysis among sample substrates on which the dummy films of different thicknesses had been formed.

2. A method of analysis of the distribution of concentration as set forth in claim 1, further including
    a step of forming on the surfaces of the sample substrates from which the dummy films have been removed buffer films of a material different from the sample substrates and
    then performing the mass analysis from the sides of the sample substrates on which the buffer films have been formed.

3. A method of analysis of the distribution of concentration as set forth in claim 2, wherein said buffer films are comprised of polycrystalline silicon films.

4. A method of analysis of the distribution of concentration as set forth in claim 2, wherein when performing said mass analysis, the primary ions are raster scanned and part of the scan region covers the region of the buffer films as well.

5. A method of analysis of the distribution of concentration as set forth in claim 1, wherein the means for introducing the impurities at the surfaces of said sample substrates is ion implantation.

6. A method of analysis of the distribution of concentration as set forth in claim 3, wherein said substrates are monocrystalline silicon substrates and said dummy films are comprised of silicon oxide films formed by thermal oxidation.

7. A method of analysis of the distribution of concentration as set forth in claim 1, wherein said dummy films comprise of a material which has a larger selectivity at the time of etching than said substrates and further gives rise to a phenomenon of introduction of impurities substantially the same as said substrates when introducing the impurities.

8. A method of analysis of the distribution of concentration as set forth in claim 1, wherein when performing said mass analysis, the primary ions are raster scanned and the substrates are made to move linearly reciprocally over the scanning direction.

9. A method of analysis of the distribution of concentration as set forth in claim 1, wherein said mass analysis is secondary ion mass analysis.

10. A method of analysis of the distribution of concentration of a substrate including:
    a step of preparing a plurality of types of sample substrates whose distribution of concentration is to be analyzed;
    a step of etching surfaces of the plurality of sample substrates to different depths;
    a step of performing destructive mass analysis from the sides of the sample substrates; and
    a step of sequentially calculating the difference in the results of said mass analysis among sample substrates having surfaces etched to different depths.

11. A method of analysis of the distribution of concentration as set forth in claim 10, further including
    a step of forming on the surfaces of the sample substrates which have been etched buffer films of a material different from the sample substrates and
    then performing the mass analysis from the sides of the sample substrates on which the buffer films have been formed.

12. A method of analysis of the distribution of concentration as set forth in claim 11, wherein said buffer films are comprised of polycrystalline silicon films.

* * * * *